(12) United States Patent
Buschulte et al.

(10) Patent No.: US 7,115,775 B2
(45) Date of Patent: Oct. 3, 2006

(54) METHOD AND DEVICE FOR THE TWO-STEP PRODUCTION OF ACRYLIC ACID

(75) Inventors: Thomas Buschulte, Kapellen (BE); Volker Diehl, Ellerstadt (DE); Bernd Hagen, Ludwigshafen (DE); Volker Huth, Neustadt (DE); Wolfgang Kasten, Ludwigshafen (DE); Peter Schlemmer, Eisenberg (DE); Axel Schroth, Grosskarlbach (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 105 days.

(21) Appl. No.: 10/474,368

(22) PCT Filed: Apr. 8, 2002

(86) PCT No.: PCT/EP02/03863

§ 371 (c)(1),
(2), (4) Date: Oct. 9, 2003

(87) PCT Pub. No.: WO02/081422

PCT Pub. Date: Oct. 17, 2002

(65) Prior Publication Data

US 2004/0138499 A1 Jul. 15, 2004

(30) Foreign Application Priority Data

Apr. 9, 2001 (DE) ................ 101 17 678

(51) Int. Cl.
*C07C 45/00* (2006.01)
*C07B 41/00* (2006.01)
(52) U.S. Cl. .............. 562/544; 562/549; 568/469.9

(58) Field of Classification Search ............. 562/523, 562/531, 532, 534, 535, 542, 544, 545, 547, 562/548, 549
See application file for complete search history.

(56) References Cited

U.S. PATENT DOCUMENTS 4,124,634 A * 11/1978 Gotoh et al. ............. 562/532
4,365,087 A  12/1982 Kadowaki et al.
2002/0037488 A1* 3/2002 Hirao et al. ............. 431/268

FOREIGN PATENT DOCUMENTS

EP 0 902 279 3/1999
EP 0 995 716 4/2000

(Continued)

*Primary Examiner*—Johann Richter
*Assistant Examiner*—Karl Puttlitz
(74) *Attorney, Agent, or Firm*—Oblon, Spivak, McClelland, Maier & Neustadt, P.C.

(57) ABSTRACT

$\alpha,\beta$-ethylenically unsaturated aldehydes and/or carboxylic acids are prepared by means of a two-stage catalytic gas-phase oxidation in which a gas mixture comprising at least an alkane or alkene having from three to six carbon atoms and oxygen is subjected to a catalytic oxidation reaction, in the first stage (1). oxygen is added to the gases produced in the first stage (1) and the resulting mixture is introduced into the second stage (2) in which it is subjected to a further catalytic oxidation reaction. In the process of the present invention, a signal which correlates with the oxygen content of the reaction gases before and/or after the addition of oxygen between the first and second stages (1, 2) is generated and the oxygen addition is regulated as a function of the signal. Also provided are an apparatus for regulating a process for preparing $\alpha,\beta$-ethylenically unsaturated aldehydes and/or carboxylic acids and an apparatus for preparing these substances using the regulating apparatus of the present invention.

4 Claims, 3 Drawing Sheets

FOREIGN PATENT DOCUMENTS

Figure 1:
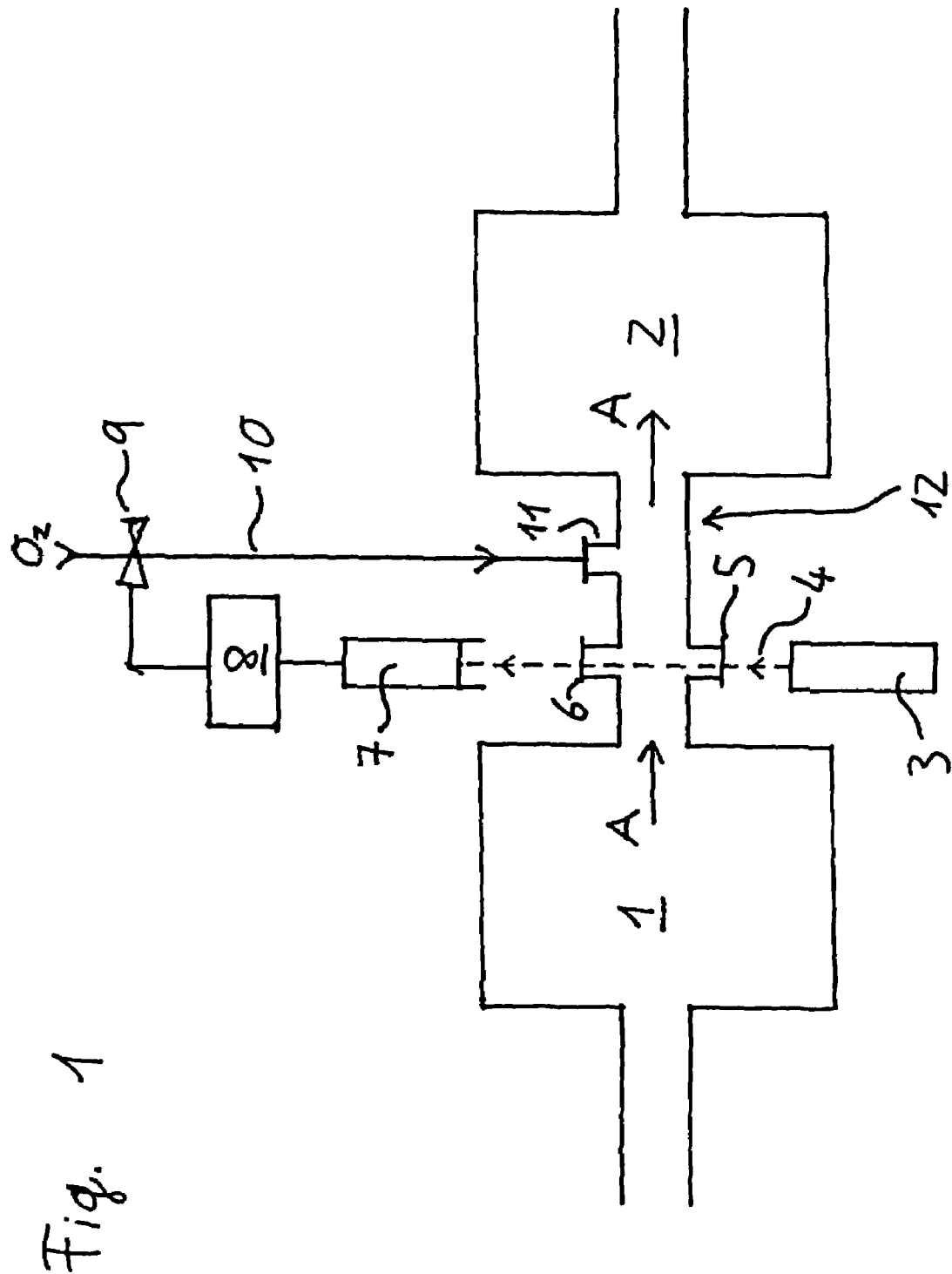

| | | |
|---|---|---|
| EP | 1 004 877 | 5/2000 |
| JP | 61-050927 | 3/1986 |
| JP | 08145921 * | 6/1996 |
| WO | 94/11622 | 5/1994 |

* cited by examiner

METHOD AND DEVICE FOR THE TWO-STEP PRODUCTION OF ACRYLIC ACID

The present invention relates in general to a process for preparing α,β-ethylenically unsaturated aldehydes and/or carboxylic acids by means of a two-stage catalytic gas-phase oxidation and in particular to a process for preparing acrylic acid. In the process, a gas mixture comprising at least an alkane and/or alkene having from three to six carbon atoms and oxygen is subjected to a catalytic oxidation reaction in the first stage, oxygen is added to the gases produced in the first stage and the resulting mixture is introduced into the second stage in which it is subjected to a further catalytic oxidation reaction. The invention further relates to an apparatus for regulating such a process and to an apparatus for preparing α,β-ethylenically unsaturated aldehydes and/or carboxylic acids.

It is known that acrylic acid can be prepared by firstly introducing propylene and molecular oxygen into the first stage. The oxygen can, for example, be introduced in the form of air. Furthermore, an inert gas such as nitrogen can be introduced. In the first stage, propylene is converted into acrolein by catalytic oxidation. The gas leaving the first stage thus comprises, inter alia, acrolein and unreacted oxygen. The gas leaving the first stage is introduced into the second stage where the acrolein and oxygen are reacted to form acrylic acid.

To convert the acrolein introduced into the second stage as completely as possible into acrylic acid, sufficient oxygen has to be available in the second stage, too. For this purpose, it is possible either to introduce such an amount of oxygen into the first stage that after the conversion of the propylene into acrolein sufficient oxygen still remains for the reaction in the second stage, or to introduce further oxygen between the first and second stages. Since increasing the proportion of oxygen in a mixture of propylene and oxygen increases the risk of explosion, it is advantageous for only that amount of oxygen which is necessary for the conversion of the propylene into acrolein to be introduced into the first stage and then for that amount of oxygen which is necessary for the conversion of the acrolein into acrylic acid to be added between the first and second stages.

However, in the industrial preparation of acrylic acid by catalytic oxidation of propylene in a first stage and subsequent conversion of the acrolein formed into acrylic acid, it is not possible to predict precisely the amount of oxygen which will be reacted in the first stage. For this reason, sufficient oxygen to ensure very complete conversion of the propylene is always introduced into the first stage. As a consequence, unreacted oxygen is always present in the gas leaving the first stage. The proportion of unreacted oxygen depends, inter alia, on the catalyst used in the first stage. Addition of further oxygen between the first and second stages results in the problem that acrolein also forms an explosive mixture with oxygen and the amount of oxygen which may safely be added is therefore restricted. For this reason, it has hitherto been the practice to add only such an amount of oxygen that a risk of explosion in the second stage can be ruled out even under unfavorable conditions, i.e. when a very high proportion of unreacted oxygen is present in the gas leaving the first stage. However, this procedure has the disadvantage that the yield of acrylic acid is reduced, since the oxygen content in the second stage under normal conditions is too low.

In addition, dynamic process states such as start-up, shutdown, throughput changes or production problems, e.g. due to malfunctions of sensors or activators, can result in the oxygen content in the second stage dropping to zero or virtually zero. In such a case, adverse effects on the catalyst cannot be ruled out.

A process for preparing acrylic acid by means of a two-stage catalytic gas-phase oxidation is described, for example, in DE 30 42 468 A1. In the process described there, the risk of explosion is overcome by means of a specific design of the reactor and a specific choice of the molar ratios of the gases introduced. To prevent an explosion in the second stage, the temperature of the gases formed in the first stage is set to a value of 280° C. or less, and in the addition of oxygen between the first and second stages, molecular oxygen and steam are homogeneously mixed with one another. The amount of molecular oxygen which is added is a fixed function of the amount of propylene introduced into the first stage.

It is an object of the present invention to provide a process for preparing α,β-ethylenically unsaturated aldehydes and/or carboxylic acids by means of a two-stage catalytic gas-phase oxidation which can be carried out safely and economically on an industrial scale. Furthermore, an apparatus for regulating a process for preparing these substances and an apparatus for preparing α,β-ethylenically unsaturated aldehydes and/or carboxylic acids are to be provided.

We have found that this object is achieved by a process as claimed in claim 1. In addition, the present invention provides an apparatus for regulating a process for preparing α,β-ethylenically unsaturated aldehydes and/or carboxylic acids as claimed in claim 5 and also an apparatus for preparing these substances as claimed in claim 11. Advantageous embodiments of this process and these apparatuses are defined in the subordinate claims.

In the process of the present invention, a gas mixture comprising at least one alkane or alkene having from 3 to 6 carbon atoms and oxygen is subjected to a catalytic oxidation reaction in the first stage. Examples of alkanes used are: propane, n-butane, isobutane, n-pentane, n-hexane. Examples of alkenes used are: propene, 1-butene, 2-butene, isobutene. Oxygen is introduced into the gases produced in the first stage and the resulting mixture is passed to the second stage in which it is subjected to a further catalytic oxidation reaction. In this way, α,β-ethylenically unsaturated aldehydes and/or carboxylic acids are produced by a two-stage catalytic gas-phase oxidation in the process of the present invention. For example, α,β-unsaturated aldehydes having from 3 to 6 carbon atoms, e.g. acrolein, methacrolein, crotonaldehyde, can be prepared. Furthermore, it is possible to prepare α,β-unsaturated carboxylic acids having from 3 to 6 carbon atoms, e.g. acrylic acid, methacrylic acid, crotonic acid. Particular preference is given to the preparation of acrylic acid and/or acrolein from propane. Also preferred are the preparation of acrylic acid from propene and the preparation of methacrylic acid or methacrolein from isobutene.

Such preparative methods are described in the following documents or the references cited therein: DE 30 02 829 A1, EP 0 293 224 B1, EP 0 911 313 A1, DE 43 08 087 A1. These documents also give further information on the reaction conditions and catalysts as also prevail or are also used in the process of the present invention. Their relevant contents are hereby incorporated by reference.

In the process of the present invention, a signal which correlates with the oxygen content of the reaction gases before and/or after the addition of oxygen between the first and second stages is generated and the oxygen addition is regulated as a function of the signal. The process of the present invention has the advantage that more oxygen for the conversion of acrolein into acrylic acid can be added between the two stages, since the amount of unreacted oxygen present in the gas leaving the first stage is known. If, for example, the proportion of oxygen which is permissible in the second stage so as to prevent an explosion is known precisely for a particular reactor for preparing acrylic acid, the process of the present invention makes it possible to add precisely that amount of oxygen which will ensure that this limit for the oxygen content is not exceeded in the second stage.

In one embodiment of the process of the present invention, the signal is generated by passing electromagnetic radiation having a wavelength at which molecular oxygen absorbs electromagnetic radiation through the gas mixture between the first and second stages before and/or after the addition of oxygen or a substream thereof and measuring the proportion of the electromagnetic radiation which has not been absorbed. An advantage of this spectroscopic measurement is that the oxygen content can be determined very accurately. Furthermore, this measurement can be carried out during the production process and it is not necessary for gas to be taken from the reactor or measuring probes to be introduced in order to carry out the measurement. In addition, the measured signal can be processed very quickly so that the addition of oxygen can be matched very well to fluctuations in the proportion of unreacted oxygen after the first stage.

The oxygen content can, for example, be measured by means of a laser beam whose wavelength is set to one of the rotational fine structure bands of molecular oxygen and which is passed through the gas mixture between the first and second stages or a substream thereof. A particularly accurate measurement of the oxygen content is possible in this way. The measurement is advantageously carried out in a wavelength range from 759.5 nm to 768 nm. The measurement is particularly preferably carried out at a wavelength of 764.76 nm (13 076.0 cm$^{-1}$). Measurement of this rotational fine structure band has a particularly low temperature dependence.

In the process of the present invention, the measurement of the oxygen content can advantageously be calibrated by passing the laser beam through a calibration cell which contains a gas having a defined oxygen content or through which a gas having a defined oxygen content is passed. The path length over which photons of the laser beam can be absorbed by the oxygen molecules present in the calibration cell, i.e. the path length of the calibration cell, is known very accurately. This makes it possible to carry out a calibration of the measurement of the oxygen content during the production process. The production process therefore does not have to be interrupted, which is advantageous.

The process of the present invention can be used particularly advantageously for preparing acrylic acid or methacrylic acid.

The apparatus of the present invention for regulating a process for preparing α,β-ethylenically unsaturated aldehydes and/or carboxylic acids by means of a two-stage catalytic gas-phase oxidation comprises a gas feed facility through which oxygen can be added to the gases produced in the first stage before they are introduced into the second stage. The apparatus comprises a measurement facility by means of which a signal which correlates with the oxygen content of the reaction gases before and/or after the addition of oxygen can be generated and the measurement facility is connected to a regulating device by means of which the amounts of oxygen added by the gas feed facility can be regulated as a function of the signal generated. As in the process described above, the regulating apparatus of the present invention has the advantage that the oxygen content of the reaction gases which are introduced into the second stage is known as a result of the measurement facility and the regulating apparatus thus makes it possible for the amount of additional oxygen which may be added without leading to a risk of explosion in the second stage to be determined accurately.

The measurement facility advantageously comprises a laser, two windows located opposite one another in the line connecting the two stages or in a bypass around this and a detector for measuring the intensity of the laser beam after passage through the line. Advantages of such a measurement facility are that it enables the oxygen content to be determined very accurately and it can be installed relatively simply in existing production plants. It is only necessary for a section of pipe having two flanges located opposite one another to be inserted between the two stages and the flanges to be sealed shut by means of windows. The laser and the detector can then be installed at the two windows. For this purpose, it is advantageous for the point of exit of the beam from the laser to be connected in a gastight manner via a tube to one window and the point of entry of the beam into the detector also to be connected in a gastight manner via a tube to the other window. It is advantageous for gaseous nitrogen to be able to be passed into and out of the tubes. In this way, the windows of the laser, the detector and the tubes and, if necessary, also the intermediate space between the windows and the laser or the detector can be freed of impurities. Furthermore, this can also compensate temperature effects arising from the environment.

In an advantageous embodiment of the apparatus of the present invention, one of the tubes is configured as a calibration cell through which or into which a gas having a defined oxygen content can be passed. In addition, it is also possible for the gas having a defined oxygen content to be introduced into the calibration cell and for the calibration measurement then to be carried out.

The surfaces of the two windows are advantageously not parallel to one another. Furthermore, these surfaces advantageously do not form a right angle with the direction of the laser beam. This prevents interference between the laser beam and itself, as a result of which an interference pattern would be superimposed over the absorption signal of the oxygen band (known as the etalon effect). This interference pattern could, depending on the thickness of the windows, become so intense that the measurement of the oxygen content would be falsified or even made impossible. For this reason, the two windows are installed obliquely and inclined in the flange so that their surfaces are no longer perpendicular to the laser beam. A deviation of only 0.5 degree from the perpendicular is sufficient here.

The laser is advantageously a modulatable diode laser whose wavelength is able to be set to one of the rotational fine structure bands of molecular oxygen in the range from 759.5 nm to 768 nm and whose modulation range is ±0.05 nm. Measurement of the rotational fine structure bands allows a particularly accurate determination of the oxygen content and the modulation of the wavelength of the laser enables the accuracy of the measurement to be increased further, since it is not just possible to evaluate the absorption at a single wavelength but instead to form an integral over a wavelength range extending from above to below the basic wavelength of the laser.

The signal which correlates with the oxygen content between the two stages is advantageously generated continuously and can be evaluated instrumentally. Such a signal is, for example, an electronic signal, a resistance change, a temperature change or a pneumatic signal. The electronic signal can comprise data in digital or analog form.

The present invention further provides an apparatus for preparing α,β-ethylenically unsaturated aldehydes and/or carboxylic acids comprising a first reaction stage and a second reaction stage connected via a connecting line to the first reaction stage and also the above-described regulating apparatus.

The invention will now be illustrated by examples with reference to the drawings.

Figure 2:
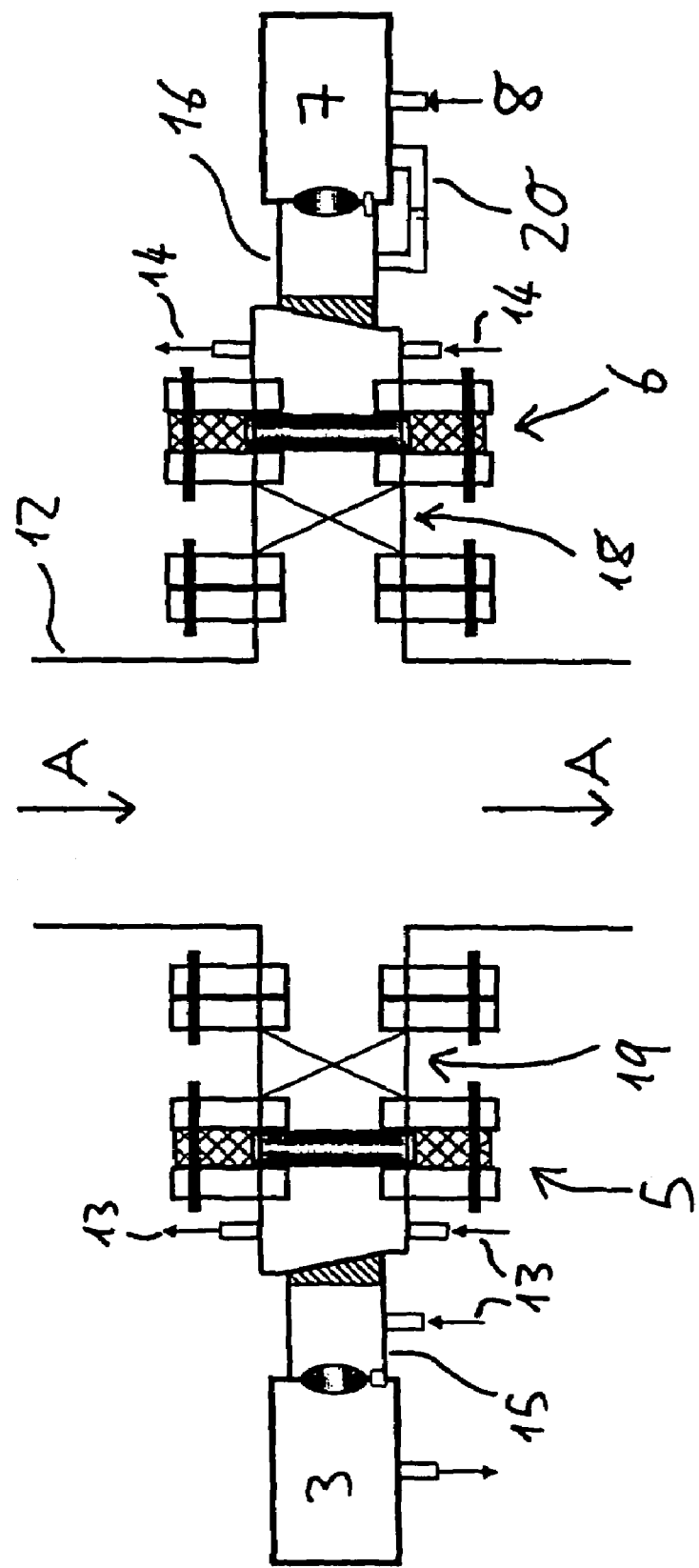
Figure 3:
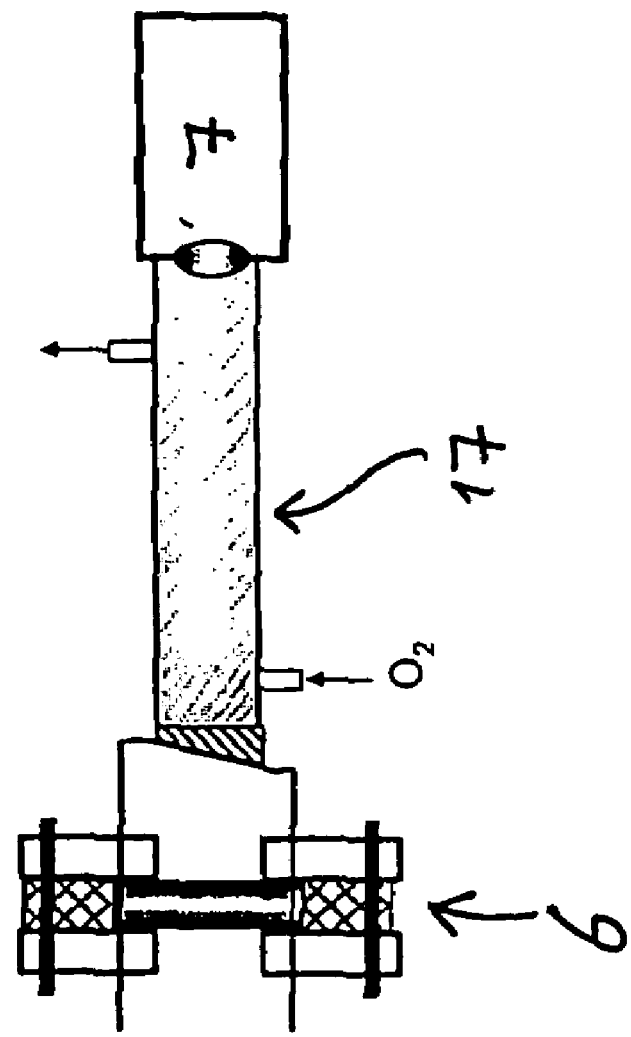

FIG. 1 schematically shows an example of the regulating apparatus of the present invention, FIG. 2 shows an embodiment of the regulating apparatus shown in FIG. 1 and FIG. 3 shows the connection of the detector 7 via a calibration cell.

The present invention will be illustrated using the preparation of acrylic acid as an example. However, it can be applied in the same way to processes or apparatuses for preparing α,β-ethylenically unsaturated aldehydes and/or carboxylic acids.

The two-stage catalytic oxidation of propylene by means of oxygen in the gas phase to form acrolein and finally acrylic acid is described in the following documents, whose relevant contents are hereby incorporated by reference: DE 30 02 829 A1, EP 0 293 224 B1, EP 0 911 313 A1, DE 43 08 087 A1. Apart from the regulation of the introduction of oxygen, the examples of the present invention can correspond to the preparative methods described in these documents.

The starting materials for the preparation of acrylic acid are introduced into the first stage 1. In stage 1, propylene and oxygen are reacted in the presence of a catalyst to form acrolein. As indicated by the arrow A in the figures, the gas leaving the first stage 1 is introduced via a connecting line 12 into the second stage 2.

The gas leaving stage 1 comprises, inter alia, acrolein and unreacted molecular oxygen. The oxygen content of this gas mixture is determined by means of a measurement facility. For this purpose, two flanges having windows 5 and 6 located opposite one another are provided in the connecting line 12. On one side of the connecting line 12, a laser 3 is installed in such a way that the emitted laser beam 4 enters through the window 5, passes through the connecting line 12 and then exits again through the window 6. On the exit side of the laser beam 4 there is a detector 7 which measures the intensity of the laser radiation which has passed through the line 12.

The windows 5 and 6 are installed in the flange so that the normals to the surfaces are at an angle of 0.5 degree to the direction of the laser beam 4. This prevents self-interference of the laser beam (known as the etalon effect, which occurs when a laser beam impinges perpendicularly on a window having parallel surfaces).

As laser 3, use is made, for example, of a modulatable diode laser model NEO Laser-Gas O2 Monitor from Norsk Elektro Optikk A/S. This laser can be set to one of the rotational fine structure bands of molecular oxygen in the range from 759.5 nm to 768 nm. For example, the measurement can be carried out at a wavelength $\lambda_0$ of 764.76 nm (13 076.0 cm$^{-1}$). This corresponds to the transition of the total angular momentum quantum number J=7 to J=6 and the transition of the rotational quantum number from N=7 to N=6. This wavelength $\lambda_0$ accordingly corresponds to a rotational level of an electronic transition of molecular oxygen. The proportion of oxygen in a gas mixture can thus be determined very specifically by measuring the absorption at this wavelength.

Owing to the doppler effect, the wavelength region in which absorptions occur is broadened as a function of the temperature of the gas mixture. Furthermore, wavelength broadening occurs as a result of collisions between molecules. For these reasons, the absorption is not measured at a particular wavelength but instead the integral $$\int_{\lambda_1}^{\lambda_2} I(\lambda)\,d\lambda$$

where $\lambda_1$ is somewhat below and $\lambda_2$ is somewhat above $\lambda_0$, is measured. The laser 3 used is modulatable for the measurement of this integral. The modulation range is about ±0.05 nm. The modulation range is, in particular, selected so that the modulation does not result in measurement of an absorption of an adjacent oxygen band.

The detector 7 converts the measured intensity of the radiation into a continuous signal which can be evaluated instrumentally and correlates with the oxygen content of the reaction gases after the first stage 1. For example, it is possible to generate an electronic signal which is proportional to the oxygen content of the gas mixture after the first stage 1.

The electronic signal is transmitted to a regulating device 8. The regulating device 8 determines the amount of additional oxygen which can be added in the second stage 2 without an explosive gas mixture being formed. The amount of oxygen to be added is calculated from the difference between the maximum oxygen content which is permitted in the second stage 2 and the oxygen content which has been measured after the first stage 1. To introduce the additional oxygen, the connecting line 12 has a further flange 11 via which gases can be fed in. In particular, the oxygen can be introduced into the connecting line 12 via the regulating valve 9 and the feed line 10. The regulating valve 9 is controlled by the regulating device 8 so that the amount of oxygen introduced into the connecting line 12 is such that the desired maximum oxygen content is achieved. It is thus possible always to introduce an amount of oxygen into the second stage 2 of the process for preparing acrylic acid which is sufficient to make virtually complete conversion of acrolein into acrylic acid possible and at the same time to rule out the formation of an explosive gas mixture.

In the embodiment of the invention shown in FIG. 2, the point of exit of the beam from the laser 3 is connected in a gastight manner via a tube 15 to the window 5 and the point of entry of the beam into the detector 7 is connected in a gastight manner via a tube 16 to the other window 6. Nitrogen can be passed through the tube 15 via the inlet and outlet lines 13 and through the tube 16 via the inlet and outlet lines 14. In this way, the windows of the laser 3 and the detector 7 and also the windows 5 and 6 of the connecting line 12 can be freed of impurities. Furthermore, ambient temperature effects can be excluded when the nitrogen gas passed through is regulated to a particular temperature. In addition, ball valves 18, 19 are provided on each side of the connecting line 12 on the line side of the windows 5, 6. When these ball valves 18, 19 are closed, the windows 5, 6 can be removed, e.g. for cleaning, without the production process having to be interrupted.

In a further embodiment of the invention, the tube 16 can be used as a calibration cell for checking the sensitivity of, i.e. calibrating, the detector 7 during the preparation of acrylic acid. For this purpose, a gas having a known oxygen concentration, e.g. air, can be introduced via line 20 into the tube 16. Furthermore, the path length traveled by the laser beam 4 in the tube 16, over which photons of the laser beam can be absorbed by oxygen molecules, is known. If it can be assumed that the oxygen content of the process gas in the connecting line 12 is constant during the time interval over which calibration of the detector 7 is carried out, the detector 7 can be calibrated by means of the known oxygen content in the tube 16.

In a further embodiment shown in FIG. 3, a dedicated calibration cell 17 can also be installed between the detector 7 and the window 6. A gas having a known oxygen content can be passed through the calibration cell 17. For example, the oxygen content in the calibration cell 17 can be increased from 0% to 100%. Provided that the oxygen content in the process gas remains constant during this time interval, the detector 7 can be calibrated in this way.

In a further example (not shown), the flanges with the windows 5 and 6 shown in FIG. 1 are interchanged with the further flange 11 for introducing the additional oxygen via line 10. This means that, viewed in the flow direction of the process gas (arrow A), oxygen is firstly introduced via line 10 and the flange 11 to the connecting line 12 and the oxygen content is then measured by means of the laser 3, the windows 5 and 6 and the detector 7. In this case, the amount of oxygen added is regulated by means of the regulating device 8 and the valve 9 so that the measured signal corresponds to the desired oxygen content for introduction into the second stage 2. An advantage of this method of operation is that the actual oxygen content upstream of the second stage 2 is measured directly. This oxygen content is the relevant parameter for the reaction, the catalyst and process safety.

In a further embodiment of the invention, it is also possible to provide a bypass parallel to the connecting line 12 and to determine the oxygen content in this bypass. For this purpose, the bypass has to be constructed so that the diverted gases have the same composition as those in the connecting line 12.

We claim:

1. A process for preparing α, β-ethylenically unsaturated aldehydes and/or carboxylic acids by means of a two-stage catalytic gas-phase oxidation in which a gas mixture comprising at least an alkane or alkene having from three to six carbon atoms and oxygen is subjected to a catalytic oxidation reaction in the first stage (1), oxygen is added to the gases produced in the first stage (1) and the resulting mixture is introduced into the second stage (2) in which it is subjected to a further catalytic oxidation reaction, wherein a signal which correlates with the oxygen content of the reaction gases before and/or after the addition of oxygen between the first and second stages (1, 2) is generated and the oxygen addition is regulated as a function of the signal.

2. A process as claimed in claim 1, wherein the signal is generated by passing electromagnetic radiation having a wavelength ($\lambda_0$) at which molecular oxygen absorbs electromagnetic radiation through the gas mixture between the first and seconds stages (1, 2) before and/or after the addition of oxygen or a substream thereof and measuring the proportion of the electromagnetic radiation which has not been absorbed.

3. A process as claimed in claim 1, wherein the oxygen content is measured by means of laser beam (4) whose wavelength is set to one of the rotational fine structure bands of molecular oxygen and which is passed through the gas mixture between the first and second stages (1, 2) or a substream thereof.

4. A process as claimed in claim 3, wherein the measurement of the oxygen content is calibrated by passing the laser beam (4) through a calibration cell (17) which contains gas having a defined oxygen content or through which a gas having a defined oxygen content is passed.

* * * * *